United States Patent
Tu et al.

[11] Patent Number: 5,971,968
[45] Date of Patent: Oct. 26, 1999

[54] CATHETER PROBE HAVING CONTRAST MEDIA DELIVERY MEANS

[75] Inventors: Hosheng Tu; Cary Hata, both of Tustin; Alan de la Rama, Cerritos, all of Calif.

[73] Assignee: Irvine Biomedical, Inc., Irvine, Calif.

[21] Appl. No.: 09/288,744

[22] Filed: Apr. 8, 1999

[51] Int. Cl.[6] .......................... A61M 5/00; A61M 29/00; A61M 37/00
[52] U.S. Cl. ........................... 604/264; 604/264; 604/95; 604/96
[58] Field of Search ................. 604/95, 96, 264

[56] References Cited

U.S. PATENT DOCUMENTS

| | | | |
|---|---|---|---|
| 4,769,006 | 9/1988 | Papantonakos | 604/95 |
| 5,431,168 | 7/1995 | Webster, Jr. | 128/658 |
| 5,487,757 | 1/1996 | Truckai et al. | 607/122 |
| 5,489,269 | 2/1996 | Aldrich et al. | 604/95 |

*Primary Examiner*—Wynn Wood Coggins
*Assistant Examiner*—Kevin C. Sirmons

[57] ABSTRACT

A catheter probe and methods for contrast media delivering comprising localized contrast media irrigation means for providing contrast media to the distal tip section, wherein the contrast media irrigation means is externally connected to a contrast media supply source; and shaft opening means for venting the contrast media out of the shaft distal end at an angle in relation to an axial reference line for optimal x-ray imaging, wherein the shaft opening means is connected to and in communication with a conduit of the contrast media irrigation means, and wherein the shaft opening means comprises at least one opening at an angle in relation to an axial reference line.

17 Claims, 5 Drawing Sheets

FIG. 3    Section A-A

CATHETER PROBE HAVING CONTRAST MEDIA DELIVERY MEANS

FIELD OF THE INVENTION

The present invention generally relates to novel constructions for a catheter probe system. More particularly, this invention relates to catheters and methods for diagnostic and ablation procedures via a steerable ablation catheter having a localized contrast media irrigation means to enhance x-ray imaging and/or fluid irrigation means for reduced impedance in a pulmonary vein resulting in a controlled lesion for treating focal atrial fibrillation.

BACKGROUND OF THE INVENTION

Symptoms of abnormal heart rhythms are generally referred to as cardiac arrhythmias, with an abnormally rapid rhythm being referred to as tachycardia. The present invention is concerned with the treatment of tachycardias which are frequently caused by the presence of an "arrhythmogenic site" or "accessory atrioventricular pathway" close to the inner surface of the chambers of a heart or in the pulmonary veins. The heart includes a number of normal pathways which are responsible for the propagation of electrical signals from the upper to the lower chambers necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to view the surrounding environment through the x-ray having contrast media enhancement and control the emission of energy to ablate the tissue within the heart or in the pulmonary veins.

Of particular interest to the present invention are radiofrequency (RF) ablation techniques that have been proven to be highly effective in tachycardia treatment while exposing a patient to minimal side effects and risks. RF catheter ablation is generally performed after conducting an initial mapping study where the locations of the arrhythmogenic site and/or accessory pathway are determined by the assistance of x-ray having contrast media. After a mapping study, an ablation catheter is usually introduced to the target heart chamber and is manipulated so that the ablation tip electrode lies exactly at the target tissue site. RF energy or other suitable energy is then applied through the tip electrode to the cardiac tissue in order to ablate the tissue of arrhythmogenic site, the accessory pathway, or the focal atrial fibrillation. By successfully destroying that tissue, the abnormal signal patterns responsible for the tachycardia may be eliminated. Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial RF ablation is inserted into a major vein or artery, usually in the neck or groin area. For focal AFib indications, a catheter is approached from the atrium to the ostium of a pulmonary vein. The tip section of a catheter is referred to hereby as the portion of that catheter shaft containing the electrode means that may be deflectable. The electrode means is to be positioned against the ostium of the pulmonary vein or preferably inside the vein, whereby the electrode means having a firm wire, a ring electrode, an orthogonal electrode, a cap electrode, a guidewire, a mesh, or coil electrode means for lesion ablation.

The impedance usually rises at the tissue contact site when RF energy is delivered through an electrode. To create a deeper and larger controlled lesion, the surface of the tissue contact sites is preferred to maintain a proper temperature by fluid irrigation means to partially compensate for the temperature rise due to RF energy delivery.

The tip section of a catheter is referred to hereby as the portion of that catheter shaft containing at least one electrode. In one embodiment, a catheter utilized in the endocardial RF ablation is inserted into a major vein or artery, usually in the neck or groin area. The catheter is then guided into an appropriate chamber of the heart by appropriate manipulation through the vein or artery. The tip of a catheter must be manipulatable by a physician from the proximal end of the catheter, so that the electrodes at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 to 8 mm in length for ablation purpose. The lesion is generally not deep because of potential impedance rise of tissue in contact with the catheter electrode and the ablation time needs to be cut short.

Accisano III in U.S. Pat. No. 5,571,085 discloses a steerable open lumen catheter, wherein the contrast media flow through a luminal conduit and vent out at an opening indiscriminately. Since contrast medium has generally a viscosity around 4 centipoises at body temperature, as compared to that for water at 0.7 centipoises, an open lumen catheter without specific flow direction would make x-ray visualization via contrast media almost worthless because of big difference in viscosity and substantial dilution of contrast media by the flowing blood. Contrast medium is hypertonic under conditions of use and may cause severe adverse events. Only adequate minimal amount should be injected for x-ray enhancement. Accisano III does not teach the usage of a minimal amount of contrast media with a directional focal injection for local x-ray enhanced visualization.

Contrast medium is also known as a diagnostic radiopaque medium. One example is iothalamate meglumine injection U.S.P., having a trade name Conray® that is manufactured by Mallinckrodt Medical. Angiography may be performed following intravascular injection that will permit general visualization until significant hemodilution occurs. To optimize contrast visualization effect, directional contrast enhancement or focal contrast enhancement at a local tissue site is extremely important in the atrial fibrillation ablation in a pulmonary vein approach. Since it is a viscous fluid, the contrast medium is preferred to be injected locally at a desired tissue site before any significant hemodilution occurs.

Therefore there is a clinical need for a new and improved catheter probe for localizing the contrast media irrigation means inside a blood vessel or an open conduit by a fluid venting opening at a substantial angle from an axial reference line and by pointing the venting opening against the local tissue site.

SUMMARY OF THE INVENTION

In general, it is an object of the present invention to provide an improved catheter probe for localized contrast media irrigation of the catheter through a distal opening at an angle relative to an axial reference line. The capability of localized contrast media irrigation applies to means of providing contrast media for x-ray viewing or imaging. It is another object of the present invention to provide a catheter probe having even fluid irrigation means for cooling off the tissue contact site due to impedance rise of an ablation electrode. This catheter probe is particularly useful for treating a patient with focal atrial fibrillation (AFib) indications in a pulmonary vein as a result of its cooled electrodes and/or delivery of controlled localized contrast media.

In one embodiment, a catheter probe for contrast media delivery comprises a catheter shaft having a shaft tip section, a shaft distal end, a shaft proximal end, and at least one lumen extending between the shaft distal end and the shaft proximal end. A handle is attached to the shaft proximal end, wherein the handle has a cavity. The catheter probe further comprises localized contrast media irrigation means for providing contrast media to the shaft tip section, wherein the contrast media irrigation means is externally connected to a contrast media supply source. The catheter probe further comprises shaft opening means for venting the contrast media out of the shaft distal end at an angle in relation to an axial reference line, wherein the shaft opening means is connected to and in communication with a conduit of the contrast media irrigation means, and wherein the shaft opening means comprises at least one opening at an angle in relation to said axial reference line for localized contrast media irrigation. The shaft opening means may comprise a plastic cap, a metal cap, or a cap electrode.

In an alternate embodiment, the catheter probe may further comprise a flap mounted at an exterior side of the at least one opening of the shaft opening means for preventing exterior fluid from backflowing into a conduit of the contrast media irrigation means.

In a preferred embodiment, a catheter probe for contrast media delivery and fluid irrigation comprises (a) a catheter shaft having a shaft tip section, a shaft distal end, a shaft proximal end, and at least one lumen extending between the shaft distal end and the shaft proximal end, wherein a cap electrode is mounted at about the shaft distal end; (b) a handle attached to the shaft proximal end, wherein the handle has a cavity; (c) contrast media irrigation means for providing contrast media to the distal tip section, wherein the contrast media irrigation means is externally connected to a contrast media supply source, and wherein the contrast media vent from a shaft opening that is connected to and in communication with the contrast media irrigation means; and (d) fluid irrigation means for providing fluid to the cap electrode, wherein the fluid irrigation means is externally connected to a fluid supply source, wherein fluid is effused out of the cap electrode, and wherein fluid irrigates and cools the cap electrode by evenly covering and rinsing the cap electrode so that an impedance rise at the contact site between the cap electrode and tissue is substantially reduced. The shaft opening of the catheter probe may be at an angle in relation to an axial reference line for localized contrast media irrigation. The angle for the shaft opening relative to the axial reference line is preferably more than 15 degrees, but less than 80 degrees.

A contrast media fluid source is positioned at one end of the catheter probe for supplying a contrast media fluid through the lumen or a separate fluid conduit inside said catheter shaft to the tip section. Therefore at mapping or ablation time, the tip section with a cap electrode is positioned against the tissues. The contrast media fluid is continuously or intermittently supplied through the opening to enhance the local tissue configuration because the opening is at an angle appropriate for the contrast medium to flow and surround the target tissue site for enhanced x-ray visualization.

The catheter probe further comprises a RF current generator, wherein the RF current generator is adapted for delivering RF current to the cap electrode through an electrical conductor. The metal cap or the cap electrode may be made of device configuration selected from the group consisting of a coil cap, a mesh cap, a peanut-shape cap, porous cap, and a liquid-permeable cap.

The metal cap or the cap electrode may be made of material selected from the group consisting of Nitinol, gold, stainless steel, silver, platinum, iridium, and an alloy of their mixtures. The configuration and construction material for a cap electrode is well known to one who is skilled in the art.

The catheter probe may further comprise at least one temperature sensor mounted on the cap electrode, wherein the catheter probe is externally equipped with a closed-loop temperature controller, and wherein the at least one temperature sensor is adapted for providing temperature sensing signals to the closed-loop temperature controller for controlling the RF current delivery. In another preferred embodiment, the catheter probe further comprises fluid control means for controlling a flow rate of contrast media through the at least one opening in association with the localized contrast media irrigation means to optimize x-ray imaging with delivery of contrast media out of the at least one opening at an angle in relation to the axial reference line, wherein the fluid control means preferably regulates the flow rate based on signals representative of x-ray exposures.

The ablation catheter further comprises a steering mechanism at the handle for controlling the deflection of said distal tip section. Usually a rotating ring or a push-pull plunger is employed in the steering mechanism. In another embodiment, the steerable ablation catheter comprises a bi-directional deflection or multiple curves deflection of the tip section. One end of the steering wire is attached at certain point of the tip section of said catheter shaft. The other end is attached to the steering mechanism at the handle. The steering mechanism on a steerable catheter or device is well known to those who are skilled in the art.

At least one electrical conductor which is secured to the cap electrode passes through the lumen of the catheter shaft and the interior void of the handle and is thereafter secured to a contact pin of the connector secured at the proximal end of the handle. Therefrom, the electrical conductor is connected to an external RF generator for ablation operations and/or to an EKG monitor for recording and display of the endocardial or epicardial electrical signal. The catheter probe system comprises a RF current generator, wherein the RF current generator is adapted for delivering RF current to the at least one electrode through an electrical conductor.

In order to provide increased torsional rigidity to the catheter shaft, the shaft material preferably comprises a polymeric tube having a Durometer in the range from 30 D to 90 D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin or anti-thrombotic substrate on the surface of the catheter shaft. It is hypothesized that the coated heparin forms a barrier, while not releasing heparin from said surface, between the blood and the catheter surface to enhance biocompatibility during electrophysiology procedures.

A method for operating a catheter probe within a cavity or a tubular organ of a patient, the method comprises the steps of (a) percutaneously introducing the catheter probe through an opening to the cavity or the tubular organ of a patient; (b) intimately contacting the cap electrode on a tissue of the cavity or the tubular organ; (c) delivering contrast media through the contrast media irrigation means for x-ray imaging, wherein contrast media are vented out of the shaft distal end at an angle in relation to an axial reference line; and (d) withdrawing the catheter probe from the patient.

The catheter system of the present invention has several significant advantages over known catheters for introducing contrast media locally to enhance x-ray visualization. In particular, the angled opening to direct the flow of contrast media to a local desired tissue site for x-ray enhancement of this invention may result in a controlled larger lesion that is highly desirable in the focal AFib treatment in a pulmonary vein. Furthermore, the contrast media irrigation means and contrast media fluid control means of the present invention may control the delivery of contrast media for x-ray viewing through the distal opening at a preferred angle in relation to an axial reference line.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE PREFERRED EMBODIMENTS

Figure 1:
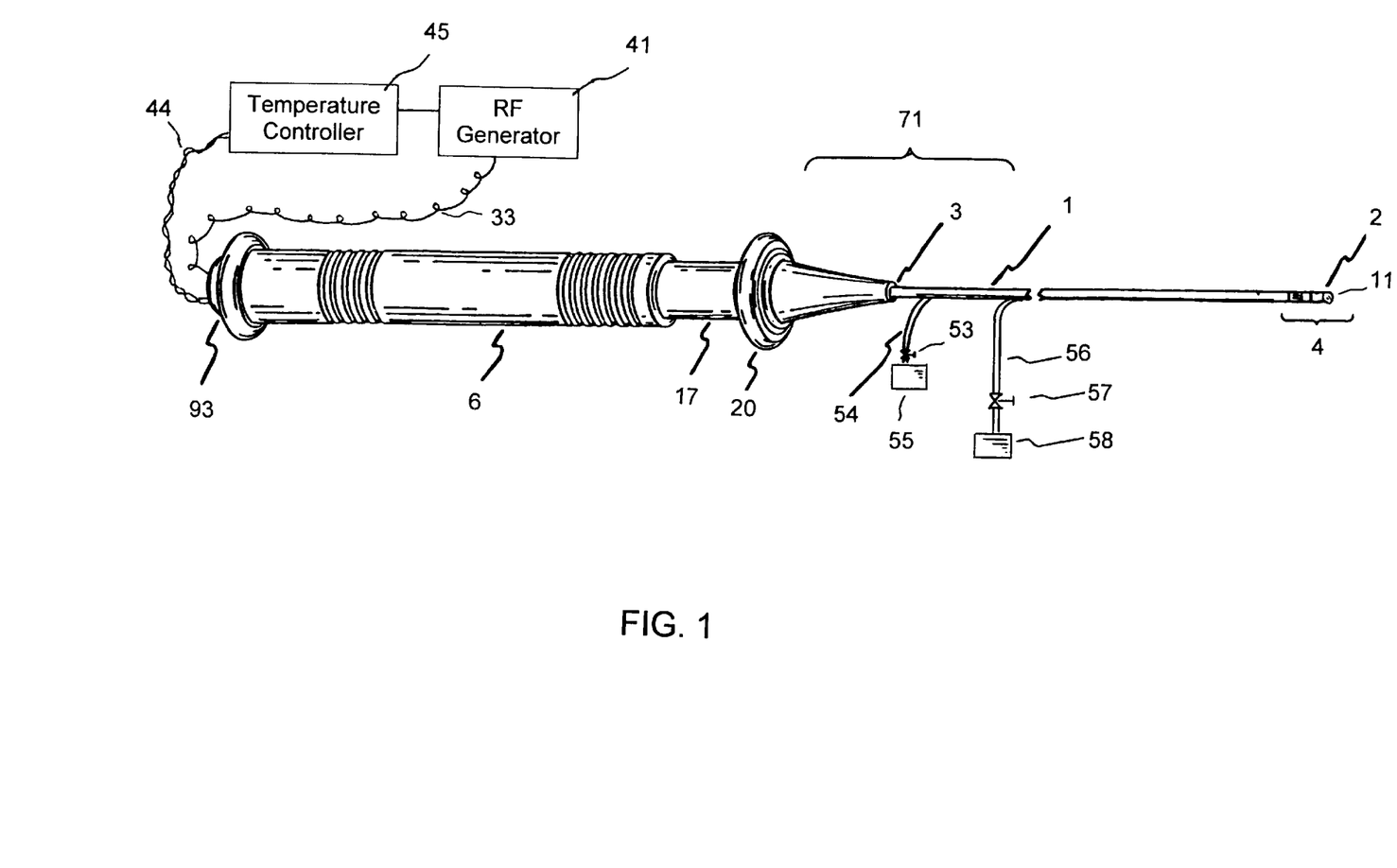
FIG. 1 is an overall view of a preferred catheter probe having contrast media irrigation means at a distal portion constructed in accordance with the principles of the present invention.

What is shown in FIGS. 1 to 5 is a preferred embodiment of the present invention. FIG. 1 shows an overall view of a preferred catheter probe having localized contrast media irrigation means at its distal portion constructed in accordance with the principles of the present invention. A catheter probe 71 comprises a catheter shaft 1 having a shaft distal tip section 4, a shaft distal end 2, a shaft proximal end 3, and at least one lumen 5 extending therebetween. In one embodiment, the catheter probe comprises contrast media irrigation means, including a control valve 57 secured to the contrast media infusion mechanism 56 that is externally connected to a contrast media supply source 58 having a pump or other pressurizing means. In an alternate embodiment, the catheter probe further comprises a fluid infusion mechanism 54 of the fluid irrigation means. A control valve 53 is secured to the fluid infusion mechanism 54 that is externally connected to a fluid supply source 55 having a pump or other pressurizing means. A handle 6 is attached to the proximal end 3 of said catheter shaft 1.

The connector 93 secured at the proximal end of the catheter probe 71, is part of the handle section 6. In one embodiment, the handle has one steering mechanism 17. The steering mechanism 17 is to deflect the tip section 4 of the catheter shaft 1 for catheter maneuvering and positioning. By pushing the front plunger 20 of the handle 6, the tip section of the catheter deflects to one direction. By pulling the front plunger 20, the tip section returns to its neutral position. In another embodiment, the steering mechanism 17 at the handle 6 comprises means for providing a plurality of deflectable curves on the distal tip section 4 of the catheter probe.

Figure 2:
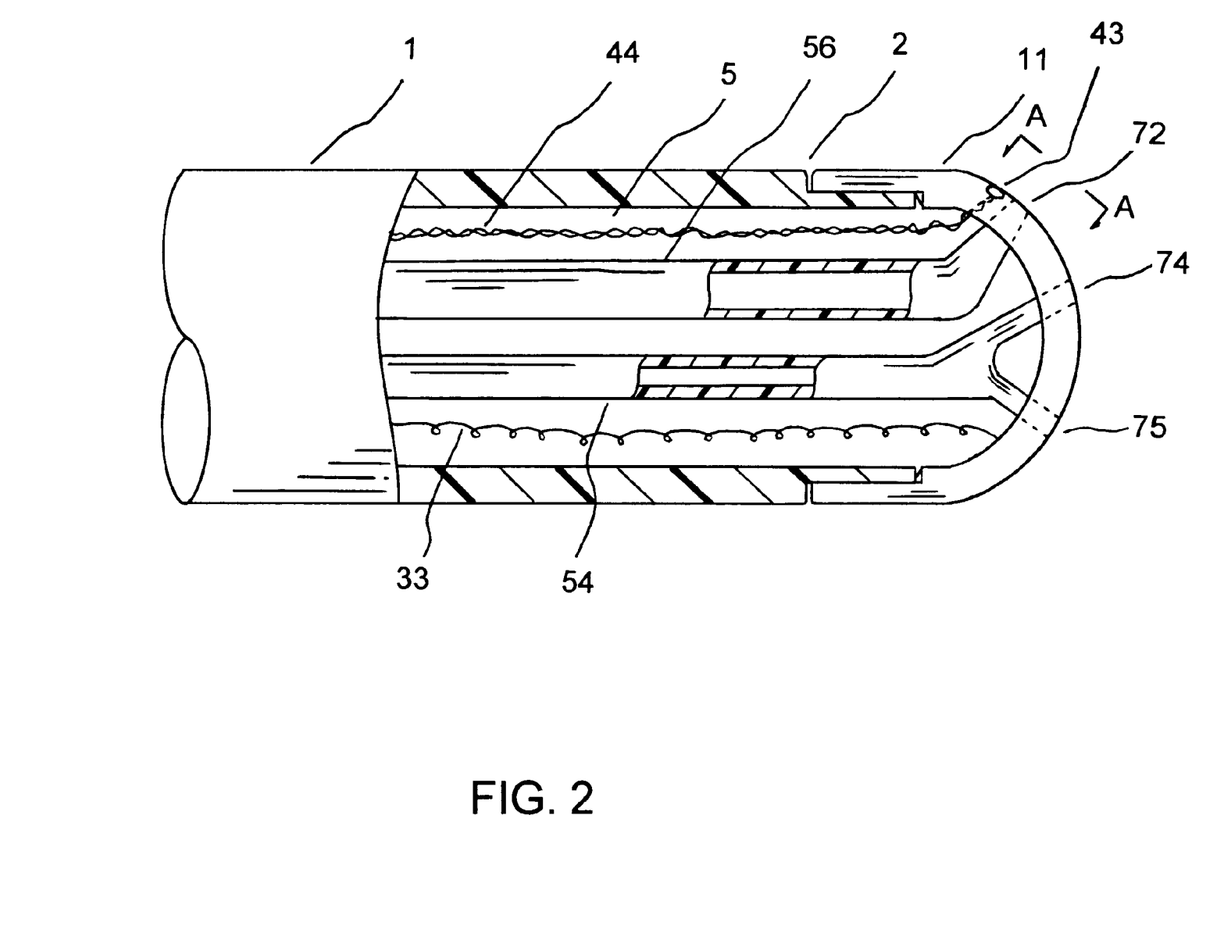
FIG. 2 is a close-up view of the distal portion of the catheter probe comprising contrast media irrigation means and fluid irrigation means.

FIG. 2 shows a close-up view of the distal portion of the catheter probe comprising localized contrast media irrigation means and fluid irrigation means. The contrast media irrigation means has contrast media conduit 56, contrast media source 58, and shaft opening means at its distal end. The shaft opening means is used for venting the contrast media out of the shaft distal end 2 at an angle in relation to an axial reference line, wherein the shaft opening means is connected to and in communication with the media conduit of the contrast media irrigation means, and wherein the shaft opening means comprises at least one opening 72 at an angle in relation to said axial reference line for localized contrast media irrigation. The angle of the at least one opening 72 is preferably more than 15 degrees and/or less than 80 degrees. In another preferred embodiment, the angle of the at least one opening is more than 45 degrees for localized contrast media irrigation. For optimal localization of the contrast media irrigation, the at least one opening 72 may be constructed to have smaller outlet mouth than its inlet mouth, wherein the inlet mouth is adjacent to a distal end of the media conduit 56.

In an alternate embodiment, the catheter probe may further comprise fluid irrigation means for providing fluid to the cap electrode 11, wherein the fluid irrigation means is externally connected to a fluid supply source 55, wherein fluid is transported via a fluid conduit 54 and effused out of the cap electrode at an opening 74. Fluid irrigates and cools the cap electrode 11 by evenly covering and rinsing the cap electrode 11 so that an impedance rise at the contact site between the cap electrode and tissue is substantially reduced. In an alternate embodiment, the fluid may also be effused out of a plurality of openings 74, 75 or out of the pores of a porous cap electrode. A porous electrode is well known to one who is skilled in the art.

Figure 3:
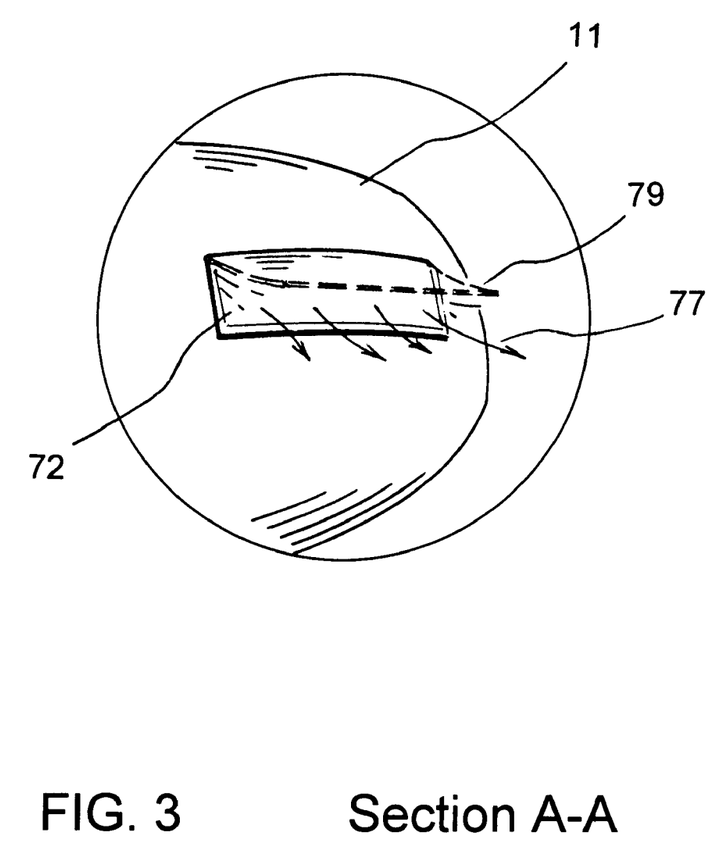
FIG. 3 is a close-up perspective view of the shaft opening portion, section A—A of FIG. 2, having a flap on top of the opening of the contrast media irrigation means.

FIG. 3 shows a close-up perspective view of the shaft opening portion, section A—A of FIG. 2, having a flap on top of the opening of the contrast media irrigation means. A flap 79 may be mounted at an exterior side of the at least one opening 72 of the shaft opening means for preventing exterior fluid from backflowing into the contrast media irrigation conduit 56. For optimal localization of the contrast media irrigation, the at least one opening 72 is constructed at an angle in relation to an axial reference line, wherein the contrast medium 77 flows toward a desired tissue site.

The catheter probe 71 comprises contrast media fluid control means 57 for controlling a flow rate of contrast media through the at least one opening 72 in association with the contrast media irrigation means to optimize x-ray imaging with delivery of contrast media 77 out of the at least one opening 72 at an angle in relation to the axial reference line, wherein the fluid control means preferably regulates the flow rate based on signals representative of x-ray exposures.

The cap electrode 11 has an insulated conducting wire 33 secured to the electrode 11, which passes through the lumen 5 of the catheter shaft 1 and is secured to a contact pin of the connector 93 at the proximal end of the handle 6. The conducting wire 33 from the connector end is externally connected to an EKG for diagnosis or to a RF generator 41 during an electrophysiology ablation procedure. Therefrom, the RF energy is transmitted through the conducting wire to the electrode and delivers the energy to the target tissue.

A temperature sensor 43, either a thermocouple means or a thermister means, is constructed at about the proximity of the electrodes 11 to measure the tissue contact temperature when RF energy is delivered. The temperature sensing wire 44 from the thermocouple or thermister is connected to one of the contact pins of the connector 93 and externally connected to a transducer and to a temperature controller 45. The temperature reading is thereafter relayed to a closed-loop control mechanism to adjust the RF energy output. The RF energy delivered is thus controlled by the temperature sensor reading or by a pre-programmed control algorithm.

Figure 4:
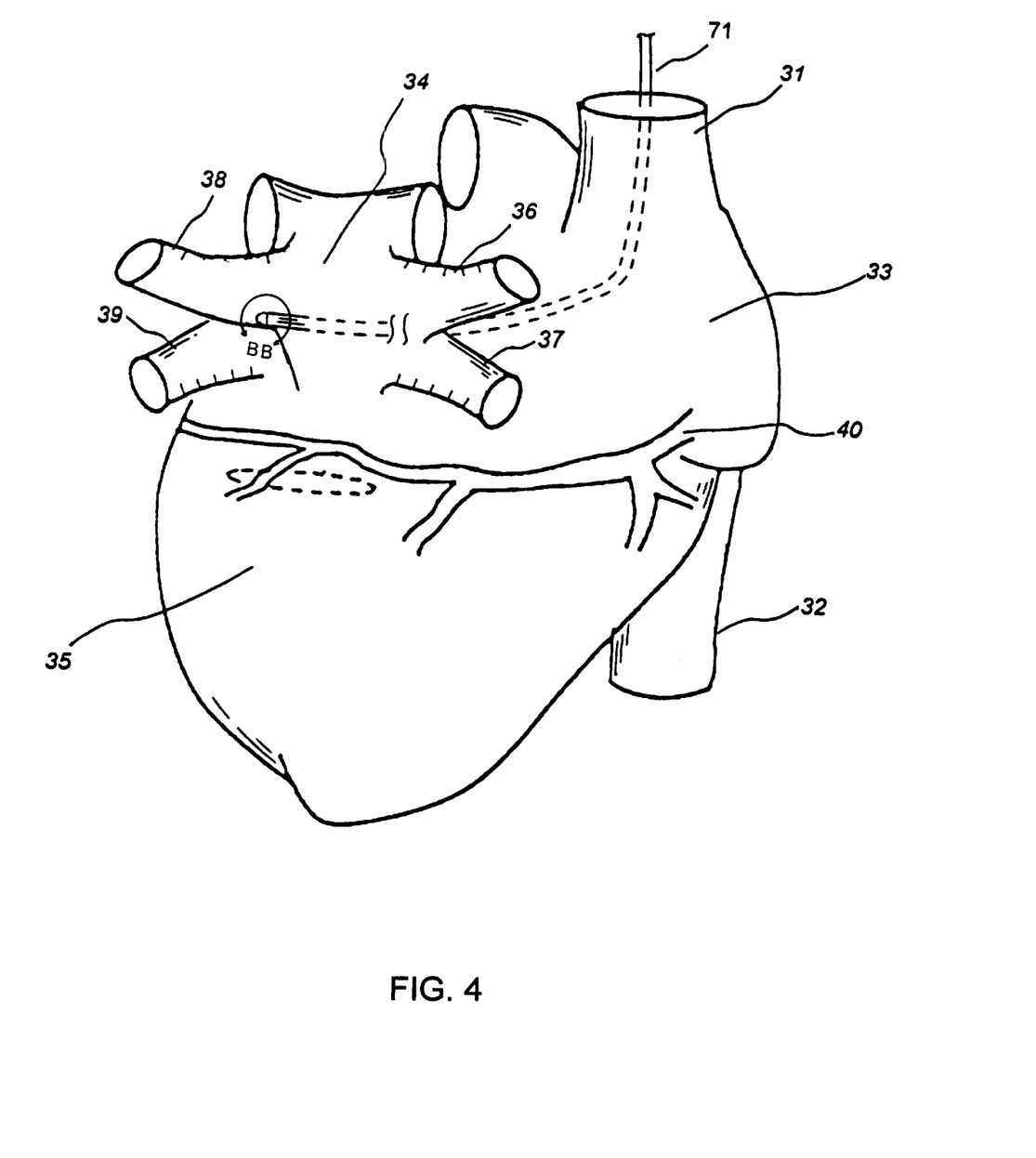
FIG. 4 is a perspective view of a catheter probe of the present invention when placed inside a pulmonary vein of the left atrium for focal atrial fibrillation treatment.
Figure 5:
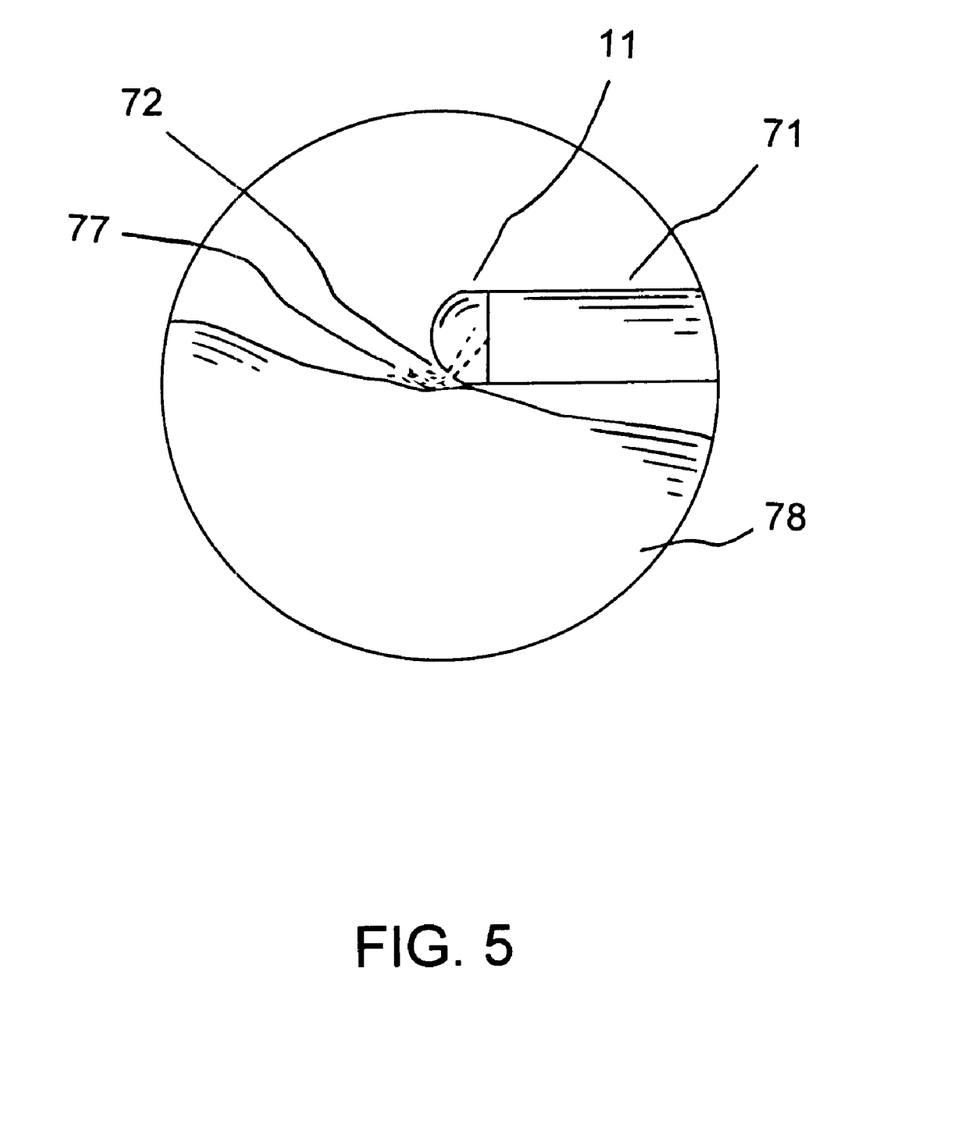
FIG. 5 is a close-up perspective view of the distal tip portion, section B—B of FIG. 4, of the catheter probe of the present invention.

FIG. 4 shows a perspective view of a catheter probe of the present invention when placed inside one pulmonary vein of the left atrium for paroxysmal atrial fibrillation treatment. To better illustrate the application of the present invention, a human heart is shown in FIG. 4. Blood returning from superior vena cava 31 or inferior vena cava 32 flows back to the right atrium 33. A coronary sinus 40 is part of the coronary artery system to provide nutrient to the epicardial heart tissue, wherein the heart also comprises a left atrium 34, a left ventricle 35 and a right ventricle. A catheter probe 71 of the present invention passing through the superior vena cava 31 into the right atrium 33. The catheter with a delivery sheath or a guiding catheter passes through the septal into the left atrium 34 for focal AFib treatment by using a standard trans-septal procedure. A normal people has four pulmonary veins: right superior pulmonary vein 36, right inferior pulmonary vein 37, left superior pulmonary vein 38, and left inferior pulmonary vein 39. In one example, a catheter probe 71 is inserted into the left atrium while its distal tip section is inserted into the left superior pulmonary vein 38. After the distal portion of the catheter probe 71 is inside the vein 38, the shaft opening 72 of the cap electrode 11 points at an acute angle toward the tissue 78. When contrast medium is injected through the angled shaft opening 72, the contrast medium is delivered locally around the tissue contact site for enhanced x-ray imaging. FIG. 5 shows a close-up perspective view of the distal tip portion, section B—B of FIG. 4, of the catheter probe of the present invention. In a preferred embodiment to have localized contrast media irrigation, the at least one opening 72 may be constructed to have smaller outlet mouth than its inlet mouth, wherein the outlet stream of the contrast media accelerates toward the target tissue 78.

In one embodiment, a method for operating a catheter probe 71 within a cavity or a tubular organ of a patient, the method comprises the steps of (a) percutaneously introducing the catheter probe through an opening to the cavity or the tubular organ of a patient; (b) intimately contacting the cap electrode on a tissue of the cavity or the tubular organ; (c) delivering contrast media through the contrast media irrigation means for x-ray imaging, wherein contrast media are vented out of the shaft distal end at an angle in relation to an axial reference line; and (d) withdrawing the catheter probe from the patient.

The method for operating a catheter probe within a cavity or a tubular organ of a patient, the catheter system further comprises a RF current generator, wherein the RF current generator is adapted for delivering RF current to the cap electrode through an electrical conductor.

From the foregoing, it should now be appreciated that an improved catheter probe having localized contrast media irrigation means and fluid irrigation means has been disclosed for electrophysiology procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter probe for contrast media delivery comprising:

a catheter shaft having a shaft tip section, a shaft distal end, a shaft proximal end, and at least one lumen extending between the shaft distal end and the shaft proximal end;

a handle attached to the shaft proximal end, wherein the handle has a cavity;

localized contrast media irrigation means for providing contrast media to the shaft tip section in a localized manner, wherein the localized contrast media irrigation means is externally connected to a contrast media supply source; and shaft opening means for venting the contrast media out of the shaft distal end at an angle in relation to an axial reference line, along a shaft lumen wherein the shaft opening means is connected to and in communication with said contrast media irrigation means, and wherein the shaft opening means comprises at least one opening having a longitudinal axis forming an angle between 15 and 80 degrees with said axial reference line for localized contrast media irrigation wherein an outlet mouth of the at least one opening is smaller than an inlet mouth of said opening.

2. A catheter probe of claim 1, wherein the shaft opening means comprises a plastic cap, a metal cap, or a cap electrode.

3. A catheter probe as in claim 2 further comprising a flap mounted at an exterior side of the at least one opening of the shaft opening means for preventing exterior fluid from backflowing into a conduct of the contrast media irrigation means.

4. A catheter probe as in claim 2 further comprising a RF current generator, wherein the RF current generator is adapted for delivering RF current to the cap electrode through an electrical conductor.

5. A catheter probe of claim 2, wherein the metal cap or the cap electrode is made of device configuration selected from the group consisting of a coil cap, a mesh cap, a peanut-shape cap, and a liquid-permeable cap.

6. A catheter probe as in claim 2, wherein the metal cap or the cap electrode is made of material selected from the group consisting of Nitinol, gold, stainless steel, silver, platinum, iridium, and an alloy of their mixtures.

7. A catheter probe as in claim 1 further comprising a steering mechanism at the handle for controlling deflection of the shaft tip section.

8. A catheter probe as in claim 4 further comprising at least one temperature sensor mounted on the cap electrode, wherein the catheter probe is externally equipped with a closed-loop temperature controller, and wherein the at least one temperature sensor is adapted for providing temperature sensing signals to the closed-loop temperature controller for controlling the RF current delivery.

9. A catheter probe as in claim 1 further comprising fluid control means for controlling a flow rate of contrast media through the at least one opening in association with the contrast media irrigation means to optimize x-ray imaging with delivery of contrast media out of the at least one opening at an angle in relation to the axial reference line, wherein the fluid control means preferably regulates the flow rate based on signals representative of x-ray exposures.

10. A catheter probe for contrast media delivery and fluid irrigation comprising:
    a catheter shaft having a shaft tip section, a shaft distal end, a shaft proximal end, and at least one lumen extending between the shaft distal end and the shaft proximal end, wherein a cap electrode is mounted at about the shaft distal end;
    a handle attached to the shaft proximal end, wherein the handle has a cavity;
    contrast media irrigation means for providing contrast media to the distal tip section in a localized manner, wherein the contrast media irrigation means is externally connected to a contrast media supply source, and wherein the contrast media vent from a shaft opening that is connected to and in communication with the contrast media irrigation means; and
    fluid irrigation means for providing fluid to the cap electrode, wherein the fluid irrigation means is externally connected to a fluid supply source, wherein fluid is effused out of the cap electrode, and wherein fluid irrigates and cools the cap electrode by evenly covering and rinsing the cap electrode so that an impedance rise at the contact site between the cap electrode and tissue is substantially reduced wherein the shaft opening is at an angle between 15 and 80 degrees in relation to an axial reference line for enhanced contrast media irrigation, wherein an outlet mouth of the at least one opening is smaller than an inlet mouth of said opening.

11. A catheter probe as in claim 10 further comprising a RF current generator, wherein the RF current generator is adapted for delivering RF current to the cap electrode through an electrical conductor.

12. A catheter probe as in claim 10 further comprising a steering mechanism at the handle for controlling deflection of the shaft tip section.

13. A method for operating a catheter probe within a cavity or a tubular organ of a patient, the catheter probe comprising a catheter shaft having a shaft tip section, a shaft distal end, a shaft proximal end, and at least one lumen extending between the shaft distal end and the shaft proximal end, wherein a cap electrode is mounted at about the shaft distal end; a handle attached to the shaft proximal end, wherein the handle has a cavity; localized contrast media irrigation means for providing contrast media to the distal tip section in a localized manner, wherein said contrast media irrigation means is externally connected to a contrast media supply source; and shaft opening means for venting the contrast media out of the shaft distal end at an angle between 15 and 80 degrees in relation to an axial reference line, wherein the shaft opening means that is connected to and in communication with a conduit of the contrast media irrigation means is located at the shaft tip section, and wherein the shaft opening means comprises at least one opening at an angle in relation to the axial reference line;
    the method comprising the steps of:
    (a) percutaneously introducing the catheter probe through an opening to the cavity or the tubular organ of a patient;
    (b) intimately contacting the cap electrode on a tissue of the cavity or the tubular organ;
    (c) delivering contrast media through the contrast media irrigation means for x-ray imaging, wherein contrast media are vented out of the shaft distal end at an angle in relation to an axial reference line; and
    (d) withdrawing the catheter probe from the patient.

14. A method for operating a catheter probe within a cavity or a tubular organ of a patient of claim 13, the catheter probe further comprising a RF current generator, wherein the RF current generator is adapted for delivering RF current to the cap electrode through an electrical conductor.

15. A method for operating a catheter probe within a cavity or a tubular organ of a patient as in claim 13, further comprising a temperature sensor mounted on about the cap electrode, wherein the catheter probe is equipped with a closed-loop temperature controller, and wherein the temperature sensor is adapted for providing temperature sensing signals to the closed-loop temperature controller for controlling the RF current delivery.

16. A method for operating a catheter probe within a cavity or a tubular organ of a patient of claim 13, wherein the catheter probe further comprising a steering mechanism at the handle for controlling deflection of the shaft tip section.

17. A method for operating a catheter probe within a cavity or a tubular organ of a patient of claim 13, wherein the catheter probe further comprising fluid control means for controlling a flow rate of contrast media through the at least one opening in association with the contrast media irrigation means to optimize x-ray imaging with delivery of contrast media, wherein the fluid control means preferably regulates the flow rate based on signals representative of x-ray exposures.

* * * * *